United States Patent [19]

Takasugi et al.

[11] Patent Number: 4,816,481
[45] Date of Patent: Mar. 28, 1989

[54] METHOD FOR IMPROVING CEREBRAL CIRCULATION

[75] Inventors: Naoyuki Takasugi; Mitsuyasu Ushijima; Satoshi Inoue; Terukage Hirata, all of Hiroshima, Japan

[73] Assignee: Wakunaga Seiyaku Kabushiki Kaisha, Osaka, Japan

[21] Appl. No.: 75,963

[22] Filed: Jul. 21, 1987

[30] Foreign Application Priority Data

Jul. 24, 1986 [JP] Japan .................. 61-174367

[51] Int. Cl.$^4$ ............................. A61K 31/365
[52] U.S. Cl. ....................... 514/470; 514/25; 549/306; 549/464; 536/18.1
[58] Field of Search ............... 549/306, 464; 536/18.1; 514/25, 469, 470

[56] References Cited

U.S. PATENT DOCUMENTS 4,103,006 7/1978 Sih ........................ 549/464
4,684,740 8/1987 Higuchi et al. ............ 549/464

FOREIGN PATENT DOCUMENTS 2849107 5/1979 Fed. Rep. of Germany .
52-102433 8/1977 Japan .

OTHER PUBLICATIONS

"The Cholinergic Hypothesis of Geriatric Memory Dysfunction", by Raymond T. Bartus et al; Science, vol. 217, Jul. 30, 1982, pp. 408–417.
"Cyclic Nucleotide Interactions Involved in Endothelium–Dependent Dilation in Rat Aortic Rings", by Geoffrey C. Grace et al; Dept. of Physiology, University of Melbourne, Parkville, Victoria 3052, Australia; 1988 Elsevier Science Pub.; pp. 17–24.
"Vasopressin Inhibition of Cyclic AMP Accumulation and Effects on the Learned Response in Inbred Mouse Strains", by Michael E. Newman and Rachel Hamburger-Bar; Life Sciences, vol. 37, pp. 2037–2042.
"Cyclic AMP Accumulation in Cerebral Cortex Tissue from Inbred Strains of Mice", by Alter Sattin; Life Science, vol. 16, pp. 903–914.
MacRae et al., Phytochemistry 23(6), pp. 1207–1220, (1984).
Brekhman et al., Lloydia, 32, pp. 46–51, (1969).
Fulder, New Scientist, pp. 576–579, (1980).
Nikaido et al., Chem. Pharm. Bull., 29(12), pp. 3586–3592, (1981).
Pelter et al., J.C.S. Perkin I, pp. 183–190, (1982).

Primary Examiner—John M. Ford
Assistant Examiner—Bernard I. Dentz
Attorney, Agent, or Firm—Oblon, Fisher, Spivak, McClelland & Maier

[57] ABSTRACT

Disclosed herein is a cerebral-circulation-metabolism-function-improving agent which contains a 2,6-diphenyl-3,7-dioxabicyclo[3.3.0]octane derivative represented by the following formula as the effective ingredient:

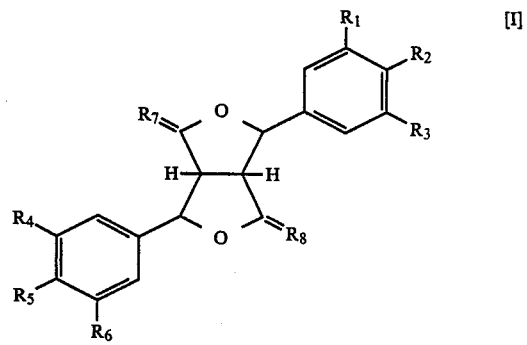

[I]

wherein, each of $R_1$, $R_3$, $R_4$ and $R_6$ represents a hydrogen atom or a lower alkoxyl group; each of $R_2$ and $R_5$ represents a hydrogen atom, a $\beta$-D-glucosyl group or a hydroxyl group; and each of $R_7$ and $R_8$ represents an oxygen atom or two hydrogen atoms.

5 Claims, 1 Drawing Sheet

METHOD FOR IMPROVING CEREBRAL CIRCULATION

BACKGROUND OF THE INVENTION

1. Field of the Invention

This invention relates to a novel use of 2,6-diphenyl-3,7-dioxabicyclo[3.3.0]octane derivatives. Specifically, this invention relates to a cerebral-circulation-metabolism-function-improving agent comprising a 2,6-diphenyl-3,7-dioxabicyclo[3.3.0]octane derivative as the effective ingredient.

2. Description of the Prior Art

Many lignans produced through condensation of cinnamyl pyrophosphate derivatives have been found in nature [Phytochemistry, 11, 1537 (1972)]. These lignans include various types of 2,6-diphenyl-3,7-dioxabicyclo[3.3.0]octane derivatives such as pinoresinol and its congeners, and piperitol and its congeners which have been isolated from crude drugs such as Chinese gutta percha, korean forsythia fruit and zanthoxylum fruit (Japanese pepper). The chemical structures of the compounds have been determined.

The pharmacological effects of such 2,6-diphenyl-3,7-dioxabicyclo[3.3.0]octane derivatives so far verified include the antihypertensive effect of 1,4-dihydroxy-1,4-bis(3,5-dimethoxy-4-hydroxyphenyl)butane-2,3-dicarboxylic dilactones and 2,6-bis(hydroxyphenyl)-3,7-dioxabicyclo[3.3.0]octane glucosides (Japanese Patent Laid-Open Sho 52-102433 and 53-7698), the carcinostatic effect, the catechol-O-methyltransferase-inhibiting effect and the adenosine-3',5'-cyclic-phosphate-phosphodiesterase-inhibiting effect of 2,6-diphenyl-3,7-dioxabicyclo[3.3.0]octane-4,8-dione derivatives and dehydrodicaffeic dilactone derivatives (Japanese Patent Laid-Open Sho 52-136193 and 54-73789), and the anticonvulsant effect, the tranquilizing effect and the antidepressant effect of sesamine and its congeners (U.S. Pat. No. 4,427,694).

As the population of aged people has greatly increased, cerebral apoplexy, cerebral infarction and senile dementia caused by cerebrovascular disorder, deterioriated nervous conduction or deteriorated energy metabolism have become a serious social problem and various types of agents have been developed (Japanese Patent Laid-Open Sho 55-17329, 59-219223 and 56-158713).

Since there is no drug for the cerebral circulation system which comprises the above 2,6-diphenyl-3,7-dioxabicyclo[3.3.0]octane derivatives and there have been no reports on the above pharmacological effects, and there is thus still room for further study of the above 2,6-diphenyl-3,7-dioxabicyclo[3.3.0]octane derivatives in the field of medicines.

SUMMARY OF THE INVENTION

This invention relates to a cerebral-circulation-metabolism-function-improving agent comprising a 2,6-diphenyl-3,7-dioxabicyclo[3.3.0]octane derivative represented by the following formula as the effective ingredient.

Accordingly, the cerebral-circulation-metabolism-function-improving agent according to this invention comprises a 2,6-diphenyl-3,7-dioxabicyclo[3.3.0]octane derivative represented by the following formula as the effective ingredient:

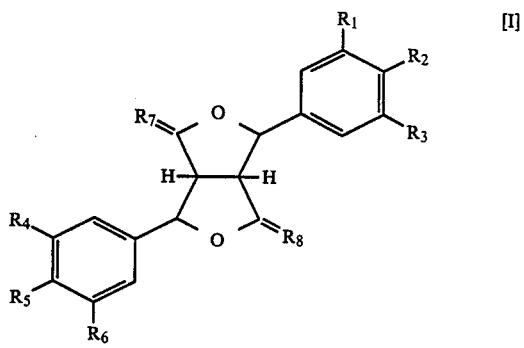

wherein, each of $R_1$, $R_3$, $R_4$ and $R_6$ represents a hydrogen atom or a lower alkoxyl group; each of $R_2$ and $R_5$ represents a hydrogen atom, a $\beta$-D-glucosyl group or a hydroxyl group; and each of $R_7$ and $R_8$ represents an oxygen atom or two hydrogen atoms.

The above physiological effect of the 2,6-diphenyl-3,7-dioxabicyclo[3.3.0]octane derivatives has been found unexpectedly and this invention providing a cerebral-circulation-metabolism-function-improving agent is believed to contribute greatly to the progress of therapy for various diseases caused by abnormal cerebral circulation or metabolism.

Figure 1:
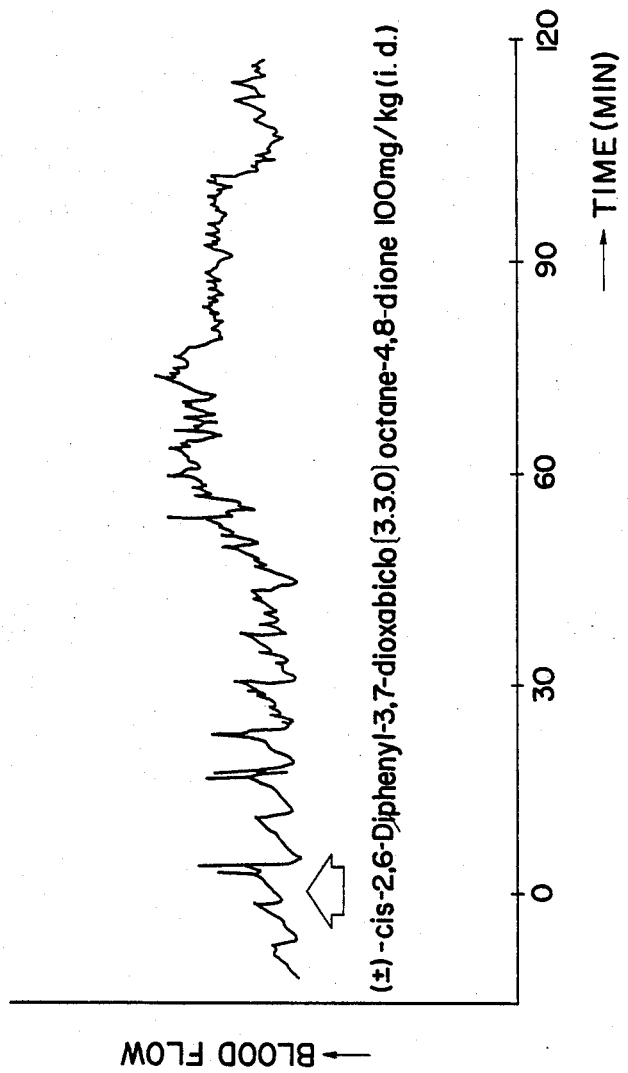
FIG. 1 indicates the cerebral-blood-stream-intensifying effect produced by administration of ($\pm$)-2,6-diphenyl-3,7-dioxabicyclo[3.3.0]octane-4,8-dione (a mixture of cis isomer and the trans isomer in a ratio of 2 to 1).

DETAILED DESCRIPTION OF THE INVENTION 2,6-Diphenyl-3,7-dioxabicyclo[3.3.0]octane derivatives The 2,6-diphenyl-3,7-dioxabicyclo[3.3.0]octane derivatives used in this invention are a compound represented by the above formula [I].

The substituents in the formula [I] are the same as those mentioned above. It is preferable that the aforementioned lower alkoxyl group contain 1-6, preferably 1-4, carbon atoms.

There are various kinds of compounds in this invention according to the types of the substituents. Some examples of these compounds are shown in the following. These compounds are examples of preferable ones and can be used as mixtures thereof.

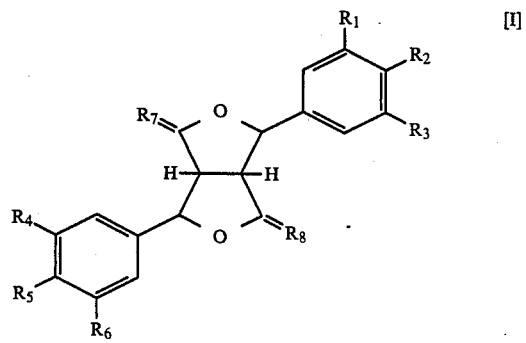

| Entry No. | R₁ | R₂ | R₃ | R₄ | R₅ | R₆ | R₇ | R₈ | Compound |
|---|---|---|---|---|---|---|---|---|---|
| 1 | OMe | O—β-Glu | OMe | OMe | O—β-Glu | OMe | 2H | 2H | Syringaresinol-di-β-glucoside |
| 2 | OMe | OH | OMe | OMe | OH | OMe | O | O | 2,6-Bis(4-hydroxy-3,5-dimethoxyphenyl)-3,7-dioxabicyclo[3.3.0]octane-4,8-dione |
| 3 | OMe | OH | H | H | OH | OMe | 2H | 2H | Pinoresinol |
|   | H | OH | OMe | OMe | OH | H | 2H | 2H |   |
| 4 | H | H | H | H | H | H | O | O | 2,6-Diphenyl-3,7-dioxabicyclo[3.3.0]octane-4,8-dione |
| 5 | OMe | OH | H | H | OH | OMe | O | O | 2,6-Bis(3-methoxy-4-hydroxyphenyl)-3,7-dioxabicyclo[3.3.0]octane-4,8-dione |
|   | H | OH | OMe | OMe | OH | H | O | O |   |
| 6 | H | H | H | H | H | H | 2H | 2H | 2,6-Diphenyl-3,7-dioxabicyclo[3.3.0]octane |
| 7 | OMe | OH | OMe | OMe | OH | OMe | 2H | 2H | Syringaresinol |

All of the above compounds are known and can be synthesized by any of well-known methods such as those specified in Tetrahedron Letters, Vol. 21, 3423 (1980), Vol. 21, 3427 (1980), Vol. 17, 1509 (1978) as well as in J. C. S., Perkin I, 183 (1982). Although each of the above compounds has optical isomers including a dextro-rotatory isomer, a levo-rotatory isomer and their mixture as well as a cis and a trans stereoisomer, all of these isomers are included in this invention.

Use of the Compound

The cerebral-circulation-metabolism-function-improving agent according to this invention is either composed of a 2,6-diphenyl-3,7-dioxabicyclo[3.3.0]octane derivative represented by the above formula [I] or prepared by mixing this compound with proper vehicle, binder or diluent for pharmaceutical preparations. This agent can be orally or parenterally administered in various forms such as a powder, granules, tablets, capsules, a syrup and an injection. Another agent may be mixed with this agent, if necessary. Although the dose of this agent should be varied according to the age, the body weight and the symptoms, the usual daily dose of a 2,6-diphenyl-3,7-dioxabicyclo[3.3.0]octane derivative per adult for oral administration is about 10 mg–20 g, preferably about 50 mg–10 g. A preferred example of this invention is composed of a 2,6-diphenyl-3,7-dioxabicyclo[3.3.0]octane derivative and an auxiliary pharmaceutical substance. Another preferred example of this invention is composed of a pharmaceutical form suitable for subdividing the above daily dose into a few doses.

The 2,6-diphenyl-3,7-dioxabicyclo[3.3.0]octane derivatives according to this invention are generally minimally toxic and no death cases have resulted from intraperitoneal administration of 2 g/kg of (±)-syringaresinol or 2,6-diphenyl-3,7-dioxabicyclo[3.3.0]octane to male mice of the ddy species.

The term "cerebral-circulation-metabolism-function-improving effect" referred to in this invention includes the cerebral-metabolism-activating effect, the cerebral-circulation-improving effect and the cerebral-function-improving effect. The cerebral-metabolism-activating effect consists of improvement of intracerebral energy metabolism. The cerebral-circulation-improving effect consists of the cerebral-blood-vessel-dilating effect and the microcirculatory-blood-stream-improving effect. The cerebral-function-improving effect consists of the effect of improving memory and learning. These effects can be pharmacologically investigated. For example, the cerebral-metabolism-activating effect can be investigated by the effect of accelerating intracerebral glucose uptake which is a reliable index. Of the cerebral-circulation-improving effect, the microcirculatory-blood-stream-improving effect can be investigated by the cerebral-blood-stream-intensifying effect which is significantly related with the microcirculatory-blood-stream-improving effect or the erythrocyte-hemolysis-inhibiting effect which is included in the blood-nature-improving effect. The cerebral-function-improving effect can be investigated by using a neurotransmission-inhibiting drug such as scopolamine to experimentally produced amnestic animal models and then observing improvement of amnesia in these models.

EXPERIMENTS

Test Animals

After male mice of the SPE and the ddy species were preliminarily bred in an animal chamber for a given period, healthy ones from these mice weighing around 25 g were subjected to this experiment. The test animals were not allowed to eat any feed from 5:00 a.m. on the day before the experiment until 10:00 on the day of the experiment.

(1) Effect of Intracerebral Glucose Uptake

Mice were orally administered with 100 mg/10 ml/kg (75 mg/kg for intraperitoneal administration) of each of the following test solutions (control, 1% gum arabic solution). Thirty minutes after administration, 8 μCi/5 ml/kg of 2-deoxyglucose-[1-$^{14}$C] was intravenously injected into the tail of each of the mice. Then, 10 minutes later, blood was collected from the mouse by section of the carotid artery and the whole brain was also collected. The blood was centrifuged at 3,000 rpm for 10 minutes and the radioactivity of the resulting plasma was measured. The whole brain was solubilized and the radioactivity of the solubilized brain was measured.

The intracerebral-$^{14}$C-uptake-accelerating effect was evaluated by obtaining the ratio between cerebral $^{14}$C(dpm/g) activity and plasma $^{14}$C(dpm/ml) activity.

(Test Solutions)

(a) 1% gum arabic (control)
(b) (±)-syringaresinol
(c) (±)-2,6-diphenyl-3,7-dioxabicyclo[3.3.0]octane (cis isomer)
(d) (±)-2,6-bis-(3-methoxy-4-hydroxyphenyl)-3,7-dioxabicyclo[3.3.0]octane-4,8-dione (cis isomer)
(e) (±)-2,6-diphenyl-3,7-dioxabicyclo[3.3.0]octane-4,8-dione (cis isomer)
(f) (±)-2,6-diphenyl-3,7-dioxabicyclo[3.3.0]octane-4,8-dione (a mixture composed of the cis and the trans isomers in a ratio of 2 to 1)

(g) (±)-2,6-diphenyl-3,7-dioxabicyclo[3.3.0]octane-4,8-dione (trans isomer)
(h) (±)-2,6-diphenyl-3,7-dioxabicyclo[3.3.0]octane-4,8-dione (cis isomer)
(i) (±)-syringaresinol-di-β-glucoside
(j) (±)-pinoresinol The results of the above experiment are shown in Table 1.

Both compounds (1) and (2) significantly accelerated the intracerebral uptake as compared with the control group. Particularly, (±)-2,6-diphenyl-3,7-dioxabicyclo[3.3.0]octane-4,8-dione produced a significant effect.

$$\text{Hemolysis rate (\%)} = \frac{\text{Complete hemolysis rate} - \text{Hypotonic hemolysis rate}}{\text{Complete hemolysis rate}}$$

(Test Solutions)
(a) 1% gum arabic
(b) (±)-syringaresinol
(c) (±)-2,6-bis(3-methoxy-4-hydroxyphenyl)-3,7-dioxabicyclo[3.3.0]octane-4,8-dione (cis isomer)
(d) (±)-2,6-bis(4-hydroxy-3,5-dimethoxyphenyl)-3,7-dioxabicyclo[3.3.0]octane-4,8-dione (cis isomer)

TABLE 1

|  | Brain $^{14}$C(Kdpm/g)/Plasma $^{14}$C(Kdpm/ml) | |
| --- | --- | --- |
|  | P.O.(100 mg/kg) | I.P.(75 mg/kg) |
| Control | 2.89 ± 0.37 | — |
| (±)-Syringaresinol | 2.99 ± 0.27 | |
| Control | 2.52 ± 0.13 | — |
| (±)-cis-2,6-Diphenyl-3,7-dioxabicyclo[3.3.0]octane | 3.10 ± 0.18 | |
| Control | 2.52 ± 0.13 | — |
| (±)-cis-2,6-Bis(3-methoxy-4-hydroxyphenyl)-3,7-dioxabicyclo[3.3.0]octane-4,8-dione | 2.59 ± 0.16 | |
| Control | 2.51 ± 0.21 | — |
| (±)-cis-2,6-Bis(4-hydroxy-3,5-dimethoxyphenyl)-3,7-dioxabicyclo[3.3.0]-octane-4,8-dione | 2.84 ± 0.26 | |
| Control | 2.52 ± 0.23 | 2.35 ± 0.16 |
| (±)-cis-,trans-2,6-Diphenyl-3,7-dioxabicyclo[3.3.0]octane-4,8-dione | 3.38 ± 0.18** | 3.01 ± 0.27 |
| Control | 2.09 ± 0.07 | — |
| (±)-trans-2,6-Diphenyl-3,7-dioxabicyclo[3.3.0]octane-4,8-dione | 2.57 ± 0.11*** | |
| Control | 2.17 ± 0.10 | — |
| (±)-cis-2,6-Diphenyl-3,7-dioxabicyclo[3.3.0]octane-4,8-dione | 2.21 ± 0.06* | |
| Control | 2.51 ± 0.21 | — |
| (±)-Syringaresinol-di-β-glucoside | 3.01 ± 0.46 | |
| Control | 2.89 ± 0.37 | — |
| (±)-Pinoresinol | 2.95 ± 0.15 | |

Student's t-test *P < 0.05, P < 0.02, *P < 0.01
mean ± S.E.(n = 6-7)

(2) Erythrocyte-hemolysis-inhibiting Effect (a) Test Animals

After male rats of the SPF and the Wistar species were preliminarily bred in an animal chamber for a given period, healthy ones from these rats weighing 240–270 g were subjected to this experiment.

(b) Method of the Experiment

Rats were orally administered with 8 ml/kg of each of the following test solutions (control, 1% gum arabic solution) successively for two days. Two days after administration, blood was collected from the descending aorta of each of the rats under ether anesthesia. Then, the blood was centrifuged to obtain erythrocytes. Next, 1 ml of the erythrocytes thus obtained was mixed with 9 ml of isotonic sodium chloride solution to prepare an erythrocyte suspension for a hypotonic hemolysis test. Next, after 200 μl of the erythrocyte suspension was mixed with 3 ml of 40 mM NaCl solution (10 mM phosphate buffer, pH 7.4) and the mixture was incubated at 37° C. for 30 minutes, the resulting mixture was centrifuged at 3,000 rpm for 10 minutes. The hemoglobin color of the supernatant thus obtained was determined by measuring its O.D. at 540 nm. For a complete hemolysis test, water was added instead of 40 mM NaCl (10 mM phosphate buffer, pH 7.4).

The hemolysis rate for administration of each test solution was calculated according to the following equation:

The results of the above experiment are shown in Table 2.

In the animals administered with compound (1) or (2), inhibition of hemolysis in a hypotonic solution was observed as compared with the control group.

TABLE 2

| Compound | Hemolysis(%) |
| --- | --- |
| Control | 60.06 ± 2.35 |
| (±)-syringaresinol | 58.32 ± 2.47 |
| (±)-cis-2,6-Bis(3-methoxy-4-hydroxyphenyl)3,7-dioxabicyclo [3.3.0]octane-4,8-dione | 55.95 ± 1.88 |
| (±)-cis-2,6-Bis(4-hydroxy-3,5-dimethoxyphenyl)-3,7-dioxabicyclo [3.3.0]octane-4,8-dione | 59.28 ± 2.25 |

(3) Learning-improving Effect (a) Method of the Experiment

Six-week old male mice of the ddy species were divided into five groups, each of which consists of 16 animals. A Step Through learning system (product of Ohara Seisakusho) equipped with a bright chamber and a dark chamber was used. Each mouse was gently placed in the bright chamber in such a manner that the tail of the mouse faced the inlet of the path and the mouse was made to challenge an acquisition trial. If the entire body of the mouse entered the dark chamber and moved across an infrared photo-beam, a foot shock of 0.4 mR was applied to the mouse. Twenty-four hours after the trial, the mouse was placed in the bright chamber and the time (latent time for the reaction) required until the mouse entered the dark chamber where the foot shock was applied and the number of mice in each group which entered the dark chamber within 500 seconds were obtained [references: (1) R. Cumin: Effects of the Novel Compound Aniracetam Upon Impared Learning and Memory in Rodents. Psychopharmacology (1982) 78: 104–111, and (2) Nobutaka Anan: A Pharmacological Study of Sufoxazine (Y-8894) (Effect on experimentally produced amnesia in mice), Folia Pharmacological Japonica 85. 71–77 (1985).] Thirty minutes before the acquisition trial, the mice were subcutaneously administered with 2 mg/kg of scopolamine used as the amnesia-inducing drug. Each of the following test agents was orally administered to mice immediately after the acquisition trial.

(Test Chemicals)

| Chemical | Dose |
|---|---|
| (a) 0.5% CMC—Na solution (control) | 10 ml/kg |
| (b) (±)-2,6-diphenyl-3,7-dioxabicyclo-[3.3.0]octane-4,8-dione (a mixture composed of the cis isomer and the trans isomer in a ratio of 2 to 1) | 1 mg/kg<br>10 mg/kg<br>100 mg/kg |
| (c) Aniracetam | 100 mg/kg |

(b) Results of the Experiment

The results of this experiment are shown in Tables 3 and 4. It was found that a small amount of (±)-2,6-diphenyl-3,7-dioxabicyclo[3.3.0]octane-4,8-dione produces an effect of improving the learning and memory of mice with scopolamine-induced amnesia.

TABLE 3

| Compound | Step through latency (sec.) |
|---|---|
| Saline(10 ml/kg,sc), 0.5% CMC—Na(10 ml/kg,po) | 300.00 ± 0.03 |
| Scopolamine(2 mg/kg,sc), 0.5% CMC—Na(10 mg/kg,po) | 235.29 ± 25.07*** |
| Scopolamine(2 mg/kg,sc), (±)-cis-2,6-diphenyl-3,7-dioxabicyclo [3.3.0]octane-4,8-dione (1 mg/kg,po) | 299.46 ± 0.54# |
| Scopolamine(2 mg/kg,sc), (±)-cis-2,6-diphenyl-3,7-dioxabicyclo [3.3.0]octane-4,8-dione (10 mg/kg,po) | 299.85 ± 0.16# |
| Scopolamine(2 mg/kg,sc), (±)-cis-2,6-diphenyl-3,7-dioxabicyclo [3.3.0]octane-4,8-dione(100 mg/kg,po) | 238.57 ± 29.99 |
| Scopolamine(2 mg/kg,sc), Aniracetam(100 mg/kg,po) | 289.46 ± 10.54# |

Mann-Whitney's U-test
Control vs. scopolamine ***p < 0.01
Scopolamine vs. compound #P < 0.05

TABLE 4

| Compound | Step through latency (%) |
|---|---|
| Saline(10 ml/kg,sc), 0.5% CMC—Na(10 ml/kg,po) | 100 |
| Scopolamine(2 mg/kg,sc), 0.5% CMC—Na(10 mg/kg,po) | 42.9*** |
| Scopolamine(2 mg/kg,sc), (±)-cis-2,6-diphenyl-3,7-dioxabicyclo [3.3.0]octane-4,8-dione(1 mg/kg,po) | 92.3# |
| Scopolamine(2 mg/kg,sc), (±)-cis-2,6-diphenyl-3,7-dioxabicyclo [3.3.0]octane-4,8-dione(10 mg/kg,po) | 84.6(#) |
| Scopolamine(2 mg/kg,sc), (±)-cis-2,6-diphenyl-3,7-dioxabicyclo [3.3.0]octane-4,8-dione(100 mg/kg,po) | 71.4 |
| Scopolamine(2 mg/kg,sc), | 84.6# |

TABLE 4-continued

| Compound | Step through latency (%) |
|---|---|
| Aniracetam(100 mg/kg,po) | |

$X^2$-test
Control vs. scopolamine ***P < 0.01
Scopolamine vs. compound (#)P < 0.10, #P < 0.05

(4) Cerebral-blood-stream-intensifying Effect (a) Method of the Experiment

Male rats of the Wistar species (weighing around 250 g) were used and each of them was immobilized with d-tubocurarine (1 mg/kg, im) and then fixed to a stereotaxic instrument under artificial respiration. Then, a plate-type blood-stream-measuring element was attached to the cerebral cortex through the parietal cranium. Next, 100 mg/kg of (±)-2,6-diphenyl-3,7-dioxabicyclo[3.3.0]octane-4,8-dione (a mixture composed of the cis isomer and the trans isomer in a ratio of 2 to 1) was intraduodenally injected and then the blood stream was measured (Takenori Yamaguchi: Effect of Boncyclane on Blood Vessels in Rat Cerebral Cortex, Clinical Study Vol. 50 No. 9 p. 2684–2689).

(b) Results of the Experiment

About 40 minutes after intraduodenal administration of 100 mg/kg of the above (±)-2,6-diphenyl-3,7-dioxabicyclo[3.3.0]octane-4,8-dione, the cerebral blood stream began to be intensified and this effect lasted up to two hours after administration (FIG. 1).

What is claimed is:

1. A method of improving cerebral circulation and metabolism which comprises administering to a patient in need of such treatment a pharmaceutically effective amount of a 2,6-diphenyl-3,7-dioxabicyclo[3.3.0]octane derivative represented by the following formula:

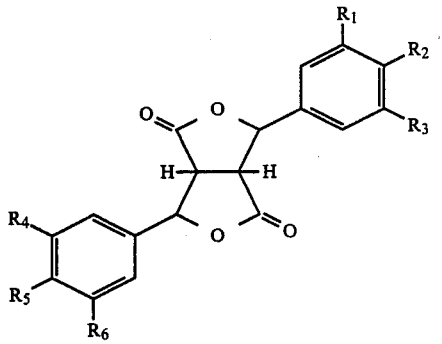

wherein, each of $R_1$, $R_3$, $R_4$ and $R_6$ represents a hydrogen atom or a lower alkoxy group and each of $R_2$ and $R_5$ represents a hydrogen atom, a -D-glucosyl group or a hydroxyl group.

2. The method as claimed in claim 1 in which the 2,6-diphenyl-3,7-dioxabicyclo[3.3.0]octane derivative is selected from the group consisting of:
(i) 2,6-bis(4-hydroxy-3,5-dimethoxyphenyl)-3,7-dioxabicyclo[3.3.0]octane-4,8-dione;
(ii) 2,6-diphenyl-3,7-dioxabicyclo[3.3.0]octane-4,8-dione;
(iii) 2,6-bis(3-methoxy-4-hydroxyphenyl)-3,7-dioxabicyclo[3.3.0]octane-4,8-dione; and
(iv) mixtures thereof.

3. The method as claimed in claim 1 in which the 2,6-diphenyl-3,7-dioxabicyclo[3.3.0]octane derivative is one wherein the substituents $R_1$ to $R_6$ are all hydrogen atoms.

4. The method as claimed in claim 1 in which the 2,6-diphenyl-3,7-dioxabicyclo[3.3.0]octane derivative is one wherein $R_1$ and $R_6$ are both $OCH_3$, $R_2$ and $R_5$ are both OH, and $R_3$ and $R_4$ are both hydrogen atoms.

5. The method as claimed in claim 1 in which the 2,6-diphenyl-3,7-dioxabicyclo[3.3.0]octane derivative is one wherein $R_1$, $R_3$, $R_4$ and $R_6$ are all $OCH_3$, and $R_2$ and $R_5$ are both OH.

* * * * *